(12) United States Patent
Liu

(10) Patent No.: US 6,411,105 B1
(45) Date of Patent: Jun. 25, 2002

(54) NONDESTRUCTIVE DETECTION OF STEEL SURFACE CORROSION

(75) Inventor: John M. Liu, Columbia, MD (US)

(73) Assignee: The United States of America as represented by the Secretary of the Navy, Washington, DC (US)

(*) Notice: Subject to any disclaimer, the term of this patent is extended or adjusted under 35 U.S.C. 154(b) by 40 days.

(21) Appl. No.: 09/659,843

(22) Filed: Sep. 11, 2000

(51) Int. Cl.[7] ................................................ G01R 27/04
(52) U.S. Cl. ...................................................... 324/639
(58) Field of Search ................................. 324/639, 328, 324/640, 637, 642, 235, 238, 232; 73/587

(56) References Cited

U.S. PATENT DOCUMENTS

| | | | | |
|---|---|---|---|---|
| 4,800,165 A | * | 1/1989 | Oka et al. ................... 324/445 |
| 4,977,377 A | * | 12/1990 | Durrett et al. ............... 324/640 |
| 5,001,434 A | * | 3/1991 | Marrelli et al. ............. 324/640 |
| 5,532,589 A | * | 7/1996 | Gammell ..................... 324/228 |
| 5,576,627 A | * | 11/1996 | Mc Ewan ..................... 324/639 |
| 5,648,038 A | * | 7/1997 | Fathi et al. .................. 324/639 |
| 5,905,376 A | | 5/1999 | Synderman et al. | |

* cited by examiner

Primary Examiner—Michael Sherry
Assistant Examiner—Anand B. Amin
(74) Attorney, Agent, or Firm—Jacob Shuster

(57) ABSTRACT

A static DC magnetic field is externally applied to a targeted surface portion of protectively coated steel to vary the amount of microwave energy absorbed therein. Measurements of varying amounts of absorbed microwave energy are compared by coordination with corresponding measurements of the strength of the applied magnetic field varied in response to coating hidden deposit of corrosion products on the targeted surface portion of the steel, to provide a basis for detection of the corrosion involved.

5 Claims, 4 Drawing Sheets

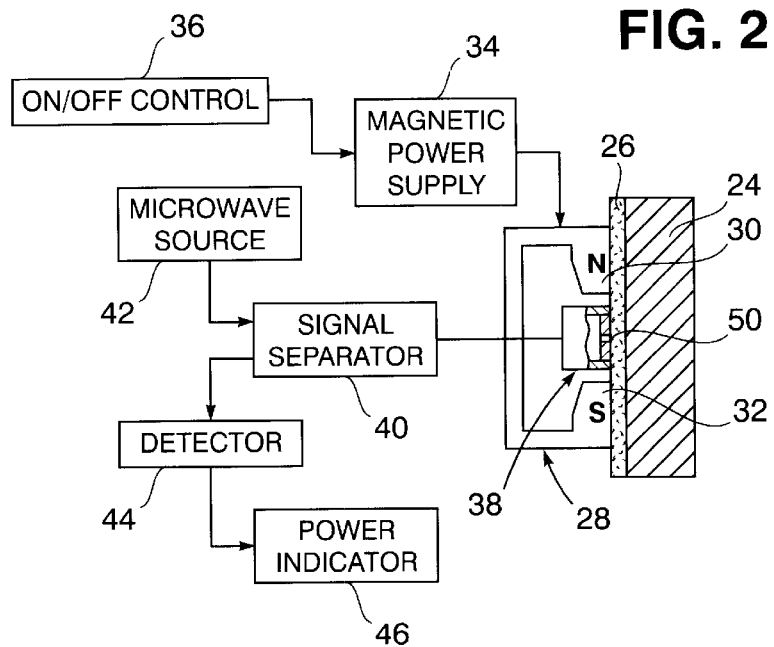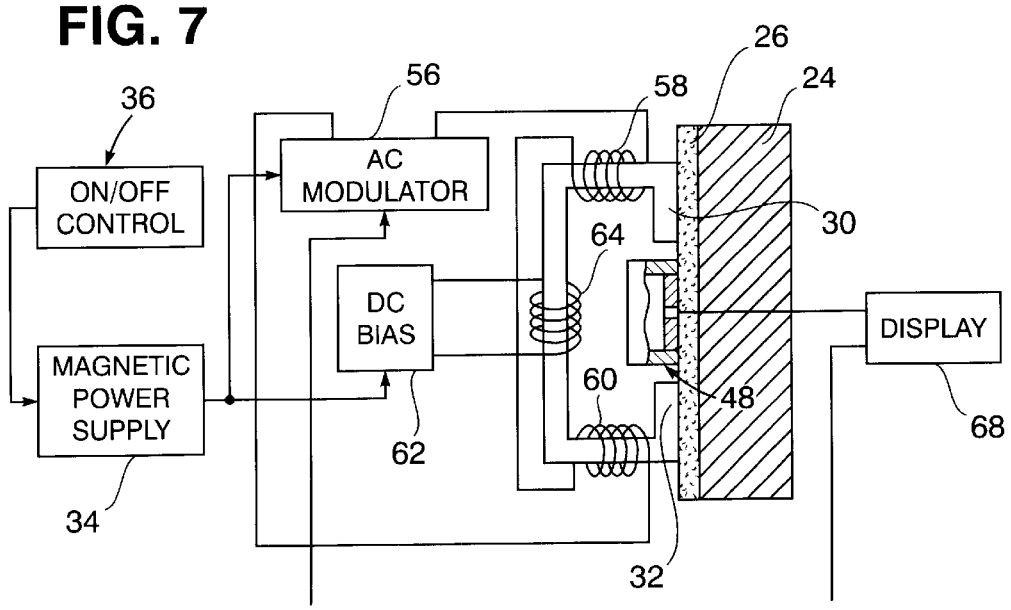

NONDESTRUCTIVE DETECTION OF STEEL SURFACE CORROSION

The present invention relates in general to the detection of corrosion on a steel surface underlying a non-magnetic coating thereon.

BACKGROUND OF THE INVENTION

The detection of corrosion underneath a protective coating on the surface of steel has been traditionally achieved by electrochemical techniques involving the use of electrolytes which render detection cumbersome and time consuming. Non-destructive evaluation techniques have also been utilized for detection of defects, involving ultrasound, eddy current, radiography or thermography reflecting changes in base metal caused by the defects. Such non-destructive evaluation techniques detect changes in mass density, elastic stiffness or conductivity of an electrical or thermal type in physically local environments of metal oxide mixtures or metal voids created by corrosion. Since typical steels have expectedly wide variations in properties associated with such local environments, it would be difficult to distinguish between such variations and those resulting from corrosion hidden underneath a coating on the steel. Also some of the foregoing existing techniques are sensitive to material thickness and geometrical effects unrelated to corrosion so as to render corrosion detection unreliable.

The detection of hidden corrosion in aluminum alloys involving use of nuclear magnetic resonance, is disclosed for example in U.S. Pat. No. 5,905,376 issued May 18, 1999. The corrosion detection technique, as disclosed in such patent, is not however applicable to steels. It is therefore an important object of the present invention to provide a reliable technique for detection of corrosion in the form of magnetic oxidation products hidden underneath a protective coating covering a targeted surface of steel.

SUMMARY OF THE INVENTION

In accordance with a corrosion detection method of the present invention, microwave energy of an appropriate frequency is absorbed in a body of steel by transmission through a protective coating on its targeted surface when a static DC magnetic field of less than 0.5 Telsa is externally applied thereto. Such absorbed microwave energy reflected from the steel body is measured through a portable sensor to provide microwave measurement data that is compared by coordination with data on variations in the strength of the magnetic field before and after corrosion of the targeted steel surface for reliable and readily available corrosion detection.

BRIEF DESCRIPTION OF DRAWING

A more complete appreciation of the invention and many of its attendant advantages will be readily appreciated as the same becomes better understood by reference to the following detailed description when considered in connection with the accompanying drawing wherein:

FIG. 2 is a partial section view and diagram depicting electronic apparatus associated with one embodiment of the system depicted in FIG. 1;

FIG. 7 diagrammatically illustrates electronic corrosion monitoring associated with another embodiment of the present invention.

DETAILED DESCRIPTION OF PREFERRED EMBODIMENTS

Figure 1:
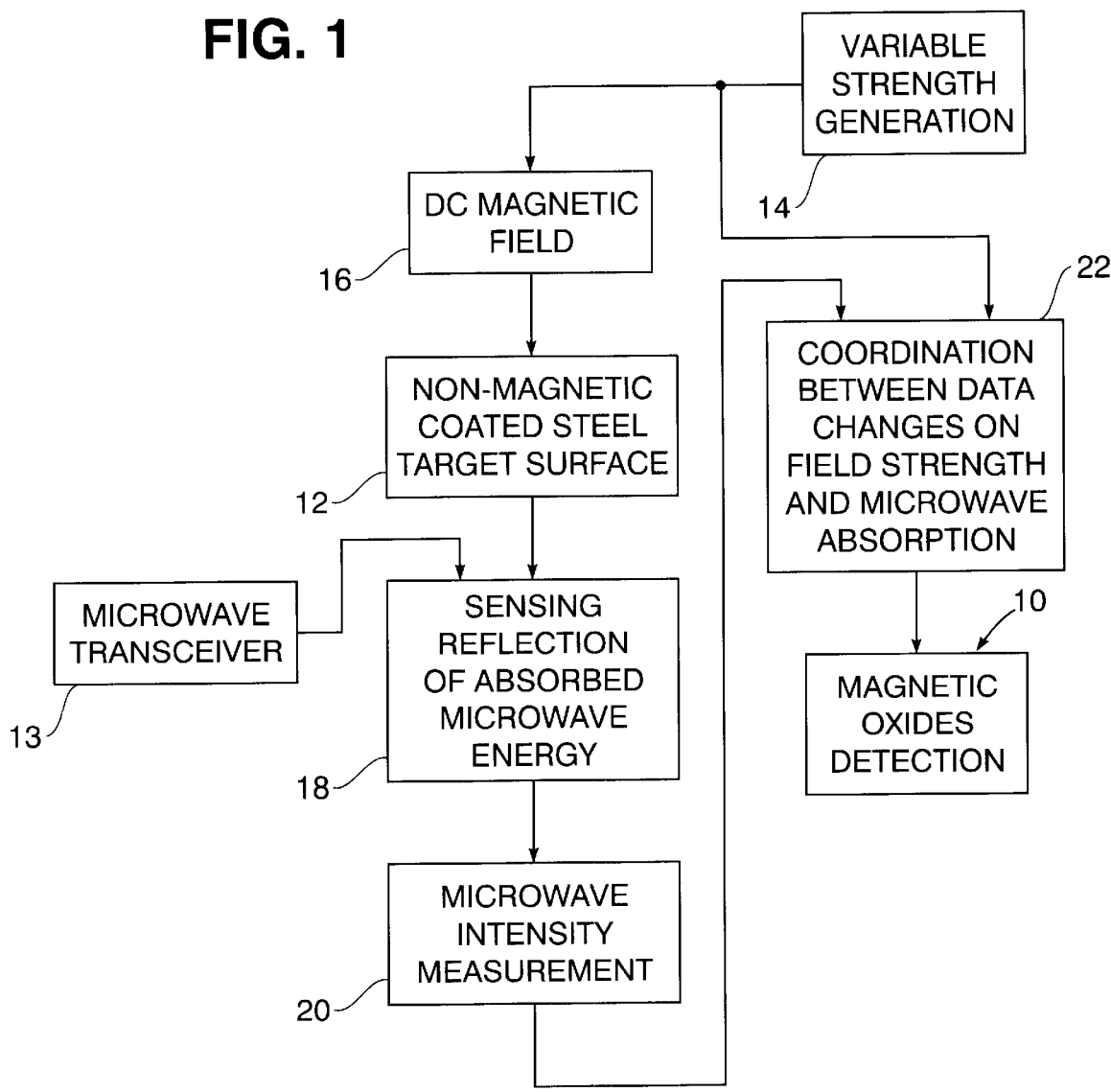
FIG. 1 is a block diagram of the corrosion monitoring system of the present invention.

Referring now to the drawing, FIG. 1 outlines a corrosion monitoring system for detection 10 of corrosion products in the form of magnetic oxides underlying a protective, non-magnetic coating on a targeted steel surface 12. The procedure associated with the corrosion monitoring system is initiated by generation 14 of variable field strength energy for a static DC magnetic field 16 externally applied to the targeted steel surface 12. Microwave energy of an appropriate frequency from a source 13 is absorbed by the steel as a result of the action of the magnetic field 16 on its target surface 12. The absorbed microwave energy then reflected from the target surface 12 undergoes sensing 18 to provide for reflected microwave intensity measurement 20. The data so obtained by the microwave intensity measurement 20 together with the value data on variable magnetic field strength of the applied magnetic field 16, produced by generation 14, are both utilized for data coordination 22 in order to provide an output as the detection 10 of the magnetic oxide corrosion products.

FIG. 2 illustrates by way of example a body of pristine steel in form of a plate 24 on which is located the targeted surface 12 denoted in FIG. 1 to be monitored for corrosion pursuant to the present invention. Such targeted surface on the steel plate 24 underlies a non-magnetic type of protective coating 26, such as paint, insulation or camouflage layers. The coating 26 hides the corrosion products which tend to form on the targeted steel surface during initial stages of corrosion or oxidation. Typical of the corrosion product magnetic oxides is magnetite ($Fe_3O_4$) having an inverted spinnel crystal structure and a permanent magnetic moment of 4 Bohr magnetrons as compared to that of iron (Fe) having a body center cubic crystal structure and an experimentally observed moment of 2.2 Bohr magnetrons. Other magnetic oxides include gamma ($Fe_2O_3$).

With continued reference to FIG. 2, an electromagnet 28 is positioned as shown on the plate 24 to externally apply the static magnetic field 16 (as denoted in FIG. 1) to the coated steel plate surface between magnet pole portions 30 and 32. Such magnetic field is induced through the electromagnet 28 in response to electrical energy fed thereto from the power supply 34. Such generation 14 of the magnetic field 16 imposes a strength thereon that is controllably varied through an on/off control 36. The strength of the static magnetic field is typically less than 0.5 Tesla so that the apparatus involved is relatively small and lightweight.

The microwave source 13 as outlined in FIG. 1, includes an antenna 38 as diagrammed in FIG. 2 focused on the plate 24 between the pole portions 30 and 32 of the electromagnet 28. The antenna 38 is connected through a signal separator 40 to a microwave energy source 42 from which the microwave energy is transmitted by the antenna 38 to the steel plate 24 at a suitable frequency and polarization entirely orthogonal to the direction of the magnetic field. Part of the microwave energy so absorbed by the material in the steel plate 24 under inducement of the magnetic field when applied, is reflected back and picked up by the same antenna 38 for direction through the signal separator 40 to a detector 44 so as to undergo the previously referred to intensity measurement 20 diagrammed in FIG. 1 through a power indicator 46 connected to the detector 44 as diagrammed in FIG. 2.

In regard to data coordination 22 as diagrammed in FIG. 1, the different magnetic properties of the pristine steel of plate 24 and the magnetic corrosion oxides deposited on its targeted surface give rise to peak absorption of the microwave energy at different strength values of the applied magnetic field to provide a basis for distinguishing between corroded steel and uncorroded steel coated for example with paint which prevents visual observation of corrosion. By choosing a value of the magnetic field strength when it is applied, which is larger than the peak value in pristine steel but smaller than the peak value for oxides, the absorbed microwave increases under the influence of the corrosion product oxides to indicate its presence by detection 10 because of the respectively different residual magnetization of the pristine steel and the magnetic oxides.

Figure 3:
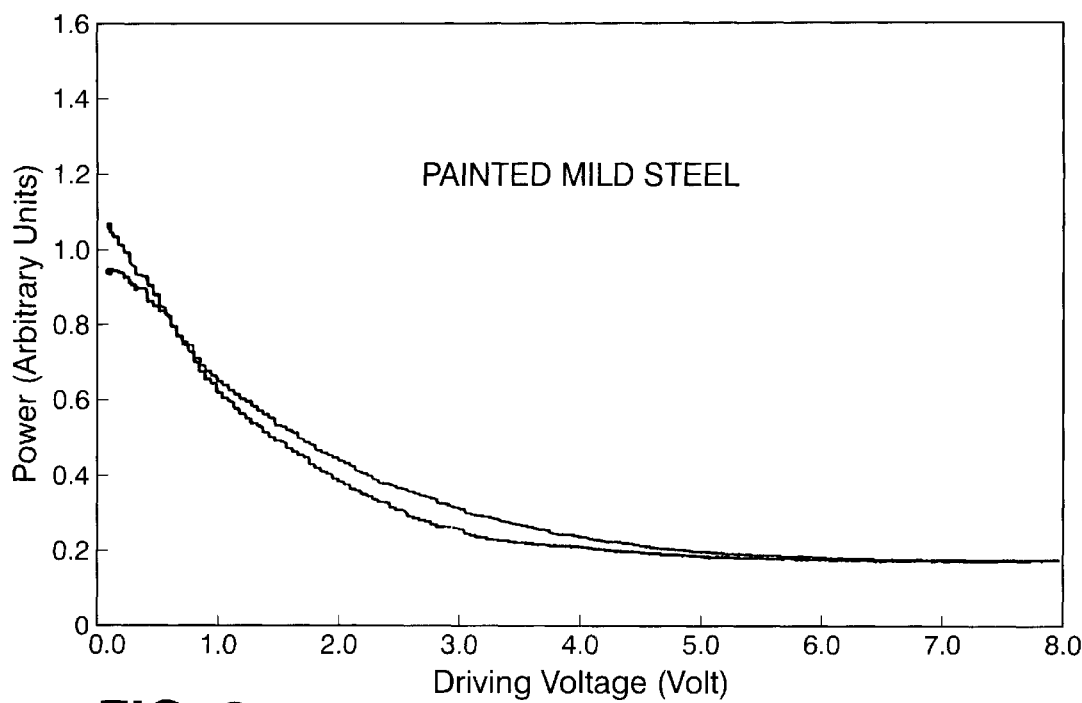
FIG. 3 is a graphical representation of absorbed microwave energy reflected from painted steel before corrosion.
Figure 4:
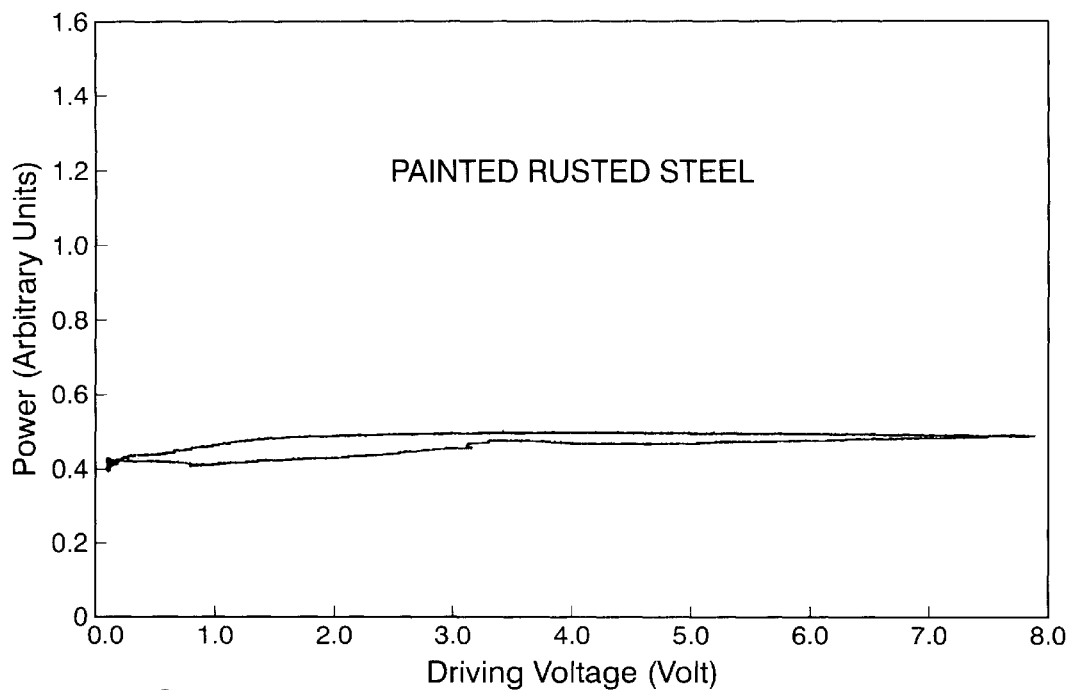
FIG. 4 is a graphical representation of absorbed microwave energy reflected from painted steel after corrosion.

FIG. 2 also diagrams use of a reflection method to sense the presence or absence of microwave absorption on the targeted surface of the steel plate 24. Antenna in the form of a portable microwave sensing resonator 38 having an aperture 50 is positioned on the targeted surface between the magnet poles 30 and 32. The measured coefficient of microwave energy reflection from such targeted surface being monitored is proportional to the differences between waveguide impedance and the impedance of the resonator 38 which varies with magnetic field applied through the magnet 28 and the presence of corrosive oxides so as to provide a more reliable basis through detection 10 for indicating corrosion as reflected by experiments conducted with a magnetic field of 0.1 Tesla applied. The results of such experiments conducted on uncorroded and corroded steel plates coated with paint, are graphically depicted in FIGS. 3 and 4 in terms of measured reflected power with a magnetic field of 0.1 Telsa applied to the pristine steel of plate 24. A comparison of the graphs in FIGS. 3 and 4 respectively associated with uncorroded and corroded steel shows an increase in the reflected power of the absorbed microwave energy when corrosion products are present.

Figure 5:
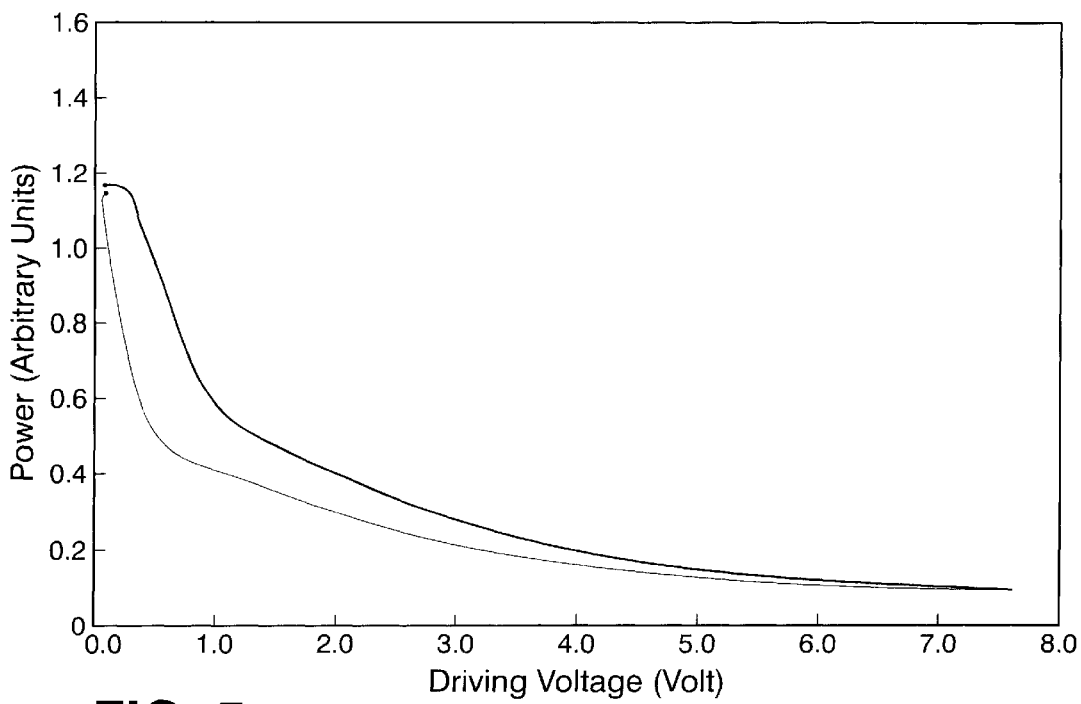
FIG. 5 is a graphical representation of microwave energy absorbed in pristine steel.
Figure 6:
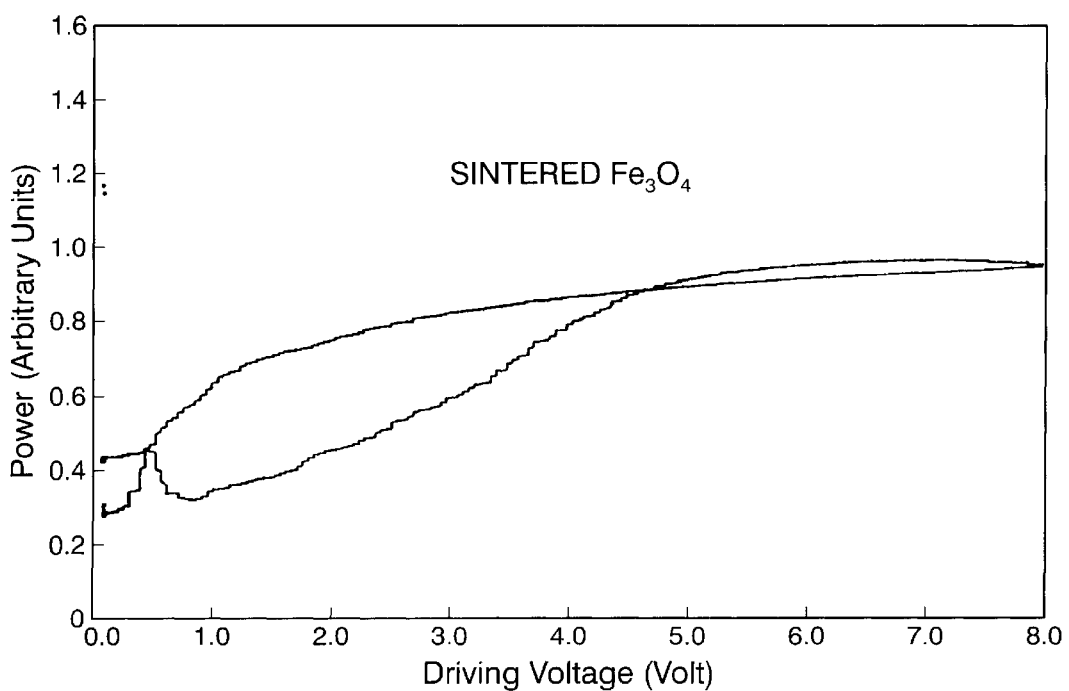
FIG. 6 is a graphical representation of microwave energy absorbed by one type of oxide (magnetite) in corrosion products.

In regard to the metal oxide corrosion products involved herein, their electrical conductivity is less than that of the pristine steel of plate 24. Also, attenuation of the microwave energy transmitted through such oxides is governed by the skin effect or thickness of the coating layer 26 so as to affect the amount of the microwave energy reaching the substrate of the steel plate 24. Since the chemistry and crystallographic nature of the steel and the corrosion oxides are very different, the amounts of microwave absorptions therein are well separated as reflected by a comparison of the experimentally derived graphs respectively depicted in FIGS. 5 and 6. Based on the foregoing referred to differences between pristine steel and corroded steel, equipment is calibrated under coordination 22 as diagrammed in FIG. 1 by use of pristine metal and magnetite sheets to provide opposite responses in electronic equipment in order to facilitate detection 10 by recognition of the distinction between pristine steel and corroded steel.

FIG. 7 diagrams a modified embodiment of the electronic system for monitoring corrosion as hereinbefore described in connection with the steel plate 24 having the coating 26 thereon, underlying the opposite pole portions 30 and 32 of the electromagnet 28 and with the resonator sensor 38 positioned thereon. Superimposed in the system with the on/off control 36 and the magnetic power supply 34 through which the DC magnetic field is generated by the magnet 28, is phase modulation involving an AC modulator 56 connected to energizing coils 58 and 60 on the electromagnet 28, also having a DC bias 62 imposed thereon through a biasing coil 64. The output of the microwave absorption sensing resonator 38 is applied to an oscilloscope display 68 and to the AC modular 56. Depending on the presence or absence of corrosion products and the nature of the base steel in plate 24, absorbed microwave radiation reflected and sensed by resonator 38 as hereinbefore described effects a change in phase of the absorbed microwave energy, which would lag the modulation imposed alone through the pristine steel of plate 24 by the signal output of AC modulator 56. This phase would be an advance of such imposed modulation when corrosion products are present, providing more readily achieved detection of corrosion products on the targeted surface of the steel plate 24. Other embodiments may similarly involve pulse modulation for enhancing detection of corrosion.

Obviously, other modifications and variations of the present invention may be possible in light of the foregoing teachings. It is therefore to be understood that within the scope of the appended claims the invention may be practiced otherwise than as specifically described.

What is claimed is:

1. A method for detection of corrosion on a surface of steel beneath a non-magnetic protective coating thereon, comprising the steps of: supplying microwave energy of appropriate frequency to the steel through said coating; externally applying a static DC magnetic field to said surface of the steel causing an amount of the transmitted microwave energy to be absorbed in the steel dependent on deposit of oxides on said surface as products of the corrosion; coordinating measurements of the amount of the microwave energy absorbed with measurements of strength of the applied magnetic field before and after said deposit of the oxides on the surface of the steel; and effecting said detection of corrosion from said coordinating of the measurements which reflect absence and presence of the said products of corrosion on the surface of the steel.

2. The method as defined in claim 1, wherein said step of applying the magnetic field includes: producing a controllable supply of electrical energy for generation of the magnetic field maintained during said application thereof to the surface of the steel; and monitoring said supply of the electrical energy to provide said measurements of the strength of the applied magnetic field.

3. The method as defined in claim 2, wherein said step of supplying the microwave energy includes: transmitting the microwave energy from an external source to a targeted portion of said surface of the steel; and receiving the absorbed microwave energy reflected through said targeted portion of the surface to provide said measurements of the amount of the absorbed microwave energy.

4. The method as defined in claim 1, wherein said step of supplying the microwave energy includes: transmitting the microwave energy from an external source to a targeted portion of said surface of the steel; and receiving the absorbed microwave energy reflected through said targeted portion of the surface to provide said measurements of the amount of the absorbed microwave energy.

5. A method for monitoring corrosion on a coated surface of steel, including the steps of: applying a magnetic field to the coated surface; transmitting microwave energy to the steel during application of the magnetic field for varying absorption in the steel of the microwave energy transmitted;

measuring said absorption of the microwave energy; measuring strength of the magnetic field during said application thereof; and coordinating the respective measurements of the magnetic field strength and said absorption of the microwave energy for detection of corrosion.

* * * * *